United States Patent
O'Shaughnessy et al.

(10) Patent No.: US 7,115,179 B2
(45) Date of Patent: Oct. 3, 2006

(54) POST-WELD NECKING OF WELDED PLASTIC JOINTS

(75) Inventors: Donagh O'Shaughnessy, Galway (IE); Alan O'Driscoll, Boston, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 54 days.

(21) Appl. No.: 10/688,298

(22) Filed: Oct. 16, 2003

(65) Prior Publication Data

US 2004/0256049 A1   Dec. 23, 2004

(51) Int. Cl.
*A61M 25/10* (2006.01)
*A61M 25/16* (2006.01)

(52) U.S. Cl. .................. 156/157; 156/159; 156/229; 604/96.01; 604/103

(58) Field of Classification Search ............... 156/157, 156/159, 229; 604/96.01, 103
See application file for complete search history.

(56) References Cited

U.S. PATENT DOCUMENTS

| | | | |
|---|---|---|---|
| 3,985,601 A | 10/1976 | Panagrossi | |
| 4,025,375 A | 5/1977 | Leasure | |
| 4,092,193 A | 5/1978 | Brooks | |
| 4,106,973 A | 8/1978 | Wright | |
| 4,251,305 A | 2/1981 | Becker et al. | |
| 4,775,371 A | 10/1988 | Mueller, Jr. | |
| 4,904,319 A * | 2/1990 | Divincenzo et al. | 156/73.4 |
| 4,990,298 A | 2/1991 | Young | |
| 5,769,819 A | 6/1998 | Schwab et al. | |
| 5,807,520 A | 9/1998 | Wang et al. | |
| 6,336,488 B1 * | 1/2002 | Vannan et al. | 152/510 |
| 6,706,010 B1 * | 3/2004 | Miki et al. | 604/43 |
| 2004/0127652 A1 * | 7/2004 | Majumdar et al. | 525/380 |

FOREIGN PATENT DOCUMENTS

| | | |
|---|---|---|
| EP | 237192 B | 3/1992 |
| EP | 483569 A | 5/1992 |
| EP | 371497 B | 10/1996 |
| GB | 1465963 | 3/1977 |
| NL | 6814117 | 12/1968 |

* cited by examiner

*Primary Examiner*—Mark A. Osele
(74) *Attorney, Agent, or Firm*—James F. Crittenden

(57) ABSTRACT

The invention relates to a method of increasing flexibility of joints between areas of plastic materials, and in particular the joint between a catheter shaft and a balloon neck involving welding the overlapping portions to create a joint region and applying a tensile force to the joint region, the force being of sufficient strength to elongate the joint region, thus thinning the joint region.

10 Claims, 2 Drawing Sheets

POST-WELD NECKING OF WELDED PLASTIC JOINTS

FIELD OF THE INVENTION

The invention relates to a method of increasing the flexibility of joints between areas of plastics materials, and in particular the joint between a catheter shaft and a balloon neck. The method also produces a reduced outside diameter in the welded region of such joints as well as a reduced cross-sectional area.

BACKGROUND TO THE INVENTION

Balloon catheters are catheters with inflatable tips which may be used to expand a partially closed or obstructed blood vessel. In such an application it is important that the catheter be as flexible as possible to allow it to travel in small blood vessels, but in prior art catheters the joint between the catheter shaft and the balloon neck tends to be relatively inflexible in the region of the welded joint.

Another problem associated with balloon catheters is that the region of the welded joint tends to swell relative to the rest of the catheter shaft. When polymers, which have their polymer chains oriented in a particular direction, are heated in order to weld two regions together, the melting temperature of the polymer is exceeded, and the polymer chains become randomised. This causes the polymer material to shrink in the direction of orientation of the polymer chains, and at the same time there is a swelling of the material in a perpendicular direction. In some applications, the resultant thickening or swelling of the joint is undesirable. One such application is in the joint between a catheter shaft and a balloon neck in an angioplasty catheter, which, because of the sensitivity of the application should be of a particular and uniform size and thus swelling in the welded area is undesirable.

There are already known in the prior art processes for forming a joint or seam between two regions of plastics material such as by heat-sealing two components of plastics materials.

U.S. Pat. No. 4,251,305 discloses a method of radiant heat-sealing of a balloon onto a catheter in which a length of tubing for forming a catheter balloon is positioned on the thermoplastic shaft of a medical device. Shrink tubing is then placed over each end of the balloon tubing and is pre-shrunk to maintain its position. Radiant heat in a narrow annular band is then applied to the shaft, the balloon tubing and the shrink tubing to seal the balloon tubing onto the shaft.

U.S. Pat. No. 4,025,375 describes a method for continuous welding of sheets into a tube with opposite sides overlapping. The sheet is tensioned longitudinally while it is heated in order to weld the material in order that the thickness of the weld region is more than twice the thickness of the original unheated sheet material.

U.S. Pat. No. 4,990,298 describes a heat shrinkable closure having a central section, which has been hot, stretched and cooled while in the stretched condition sandwiched between a pair of unstretched end sections and in which one end section has a tapered grooved extension. The hot stretching followed by cooling renders that portion of the material heat-shrinkable.

U.S. Pat. No. 4,775,371 describes a method of manufacturing a stiffened dilation catheter. The catheter has a relatively stiff proximal end portion, which is formed by bonding a stiff tubular member coaxially with the proximal end portion of the relatively soft outer tubular member. The distal end portions of the inner and outer tubular members are sealed together to close the distal end of the balloon. A mandrel is inserted into the relatively stiff tubular member, which is then heated and pulled to shrink it down about the mandrel, thereby reducing the wall thickness of the member.

U.S. Pat. No. 3,985,601 discloses a method for producing an inflatable balloon catheter having an inflatable catheter tip attached to a double lumen catheter shaft to form a smooth continuous outer surface at the outer juncture of the tip and shaft. The catheter shaft has an initial outside diameter approximately equal to the outside diameter of the balloon section, and while in a partially cured state, a leading portion of the extruded shaft is stretched to locally reduce its outside diameter. The entire shaft is then cured.

U.S. Pat. No. 5,769,819 discloses a medical catheter comprising a guide wire shaft defining a guide wire lumen. The catheter has a distal tip extension with a reduced outer diameter to which a balloon is attached. The distal tip extension is tapered at one end by shaving, by radio frequency welding or by compressive heat bonding.

U.S. Pat. No. 4,092,193 describes a coupling means for joining substrates such as tubular articles. The tubular articles include an inner member having a fusable agent and an outer member. The substrates to be joined are inserted between the fusable agent and the outer member and the resulting assembly is heated. The heat raises the temperature of the fusable agent enough so that it melts and flows through and/or about the substrates to be joined with the inner and outer members acting to confine the melted fusable agent by defining boundaries between which it can flow. This bonds the two tubular articles together.

EP-B-371 497 discloses a urethra catheter, which is made by attaching a balloon to the end of a catheter shaft, heating the end portions of the balloon to weld them to the shaft and then machining the shaft tube. The front-end portion of the catheter shaft is reduced in diameter and the balloon is welded to the portion of the shaft having a reduced diameter.

EP-A-483 569 discloses a plastic welding apparatus for sealing a first plastic material to a second plastic material using a laser beam.

EP-B-237 192 discloses a method for welding together plastic or plastic covered surfaces with the aid of laser beam heating.

U.S. Pat. No. 5,807,520 discloses a method of balloon formation involving the steps of extruding a segment of thermoplastic material, maintaining the centre portion at a temperature blow the glass transition temperature of a thermoplastic material, drawing the segment to a pre-determined length, in which, after drawing, the wall thickness of the centre portion does not appreciably change, and then expanding the segment in a mould to produce the balloon.

While many processes are known for welding together joints of plastic material as described above, one problem with the prior art process is that the cross-sectional area of the welded region is greater than the cross-sectional area of the adjoining regions. This creates a swollen area in the weld region, which is unsuitable for many applications. No prior art document teaches a process in which two polymeric materials are first heat-sealed together and the joint is then stretched.

OBJECT OF THE INVENTION

It is an object of this invention to provide a process, which produces a more flexible joint between welded areas of plastics materials. It is a further object to produce a weld between areas of plastics materials, which has a reduced outside diameter. A still further object is to provide a process, which reduces the cross-sectional area of the welded region between two portions of plastics material. It is a further object to eliminate swelling in the welded joint region between the two portions.

SUMMARY OF THE INVENTION

According to the present invention there is provided a process for forming a joint between two overlapping portions of polymeric material, comprising welding the overlapping portions to create a joint region and applying a tensile force to the joint region, the force being of sufficient strength to elongate the joint region, thus thinning the joint region.

The two overlapping portions may be heat welded together. The tensile force is suitably a stretching force. The tensile force may be applied to a cold joint or to a joint, which is being heated. Heating may be achieved by the application of hot air.

The process finds particular application in the production of catheter shafts and balloons, wherein the two overlapping portions of polymeric material are a catheter shaft and a balloon neck.

Suitably, the balloon neck is clamped adjacent the joint region between the catheter shaft and the balloon neck and the tensile force is applied between the clamped regions. Suitably, the balloon neck is clamped on either side of the joint region and the tensile force is applied between the clamped regions.

BRIEF DESCRIPTION OF THE DRAWINGS

The invention will now be described in greater detail with reference to the accompanying drawings in which.

DETAILED DESCRIPTION OF THE DRAWINGS

Figure 1:
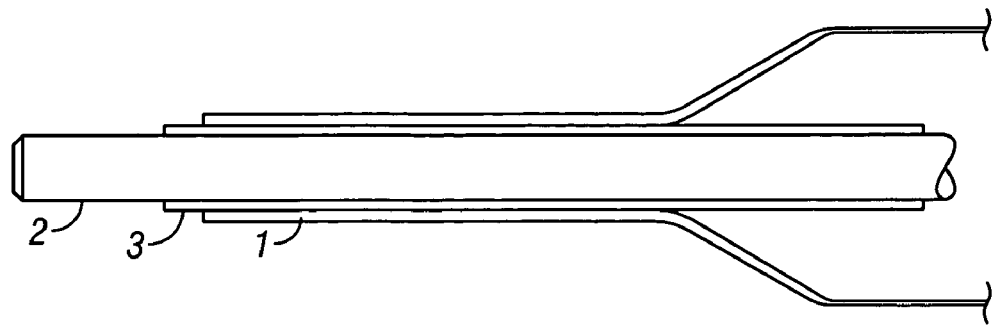
FIG. 1 shows a catheter shaft and balloon.
Figure 2:
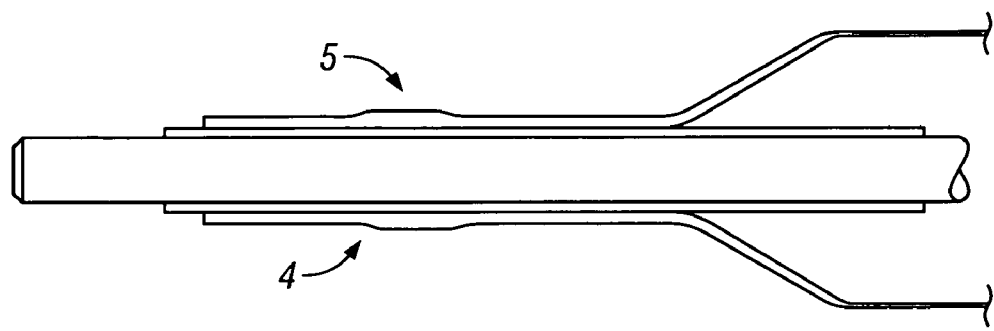
FIG. 2 shows a catheter shaft and balloon following heat welding of the shaft to the balloon.

As shown in FIG. 1, an angioplasty balloon (1) is mounted on a mandrel (2) together with a polymer shaft (3). The balloon (1) and the shaft (3) are then welded together in the balloon neck area (4) by conventional means in order to effect a fluid-tight seal. The conventional welding process applies heat, from a heat source, which can cause the material to swell radially in the weld zone. This is shown in greater detail in FIG. 2. In prior art procedures, this radial swelling (5) has been minimised by the use of an external mould or a heat-shrink sleeve.

Figure 3:
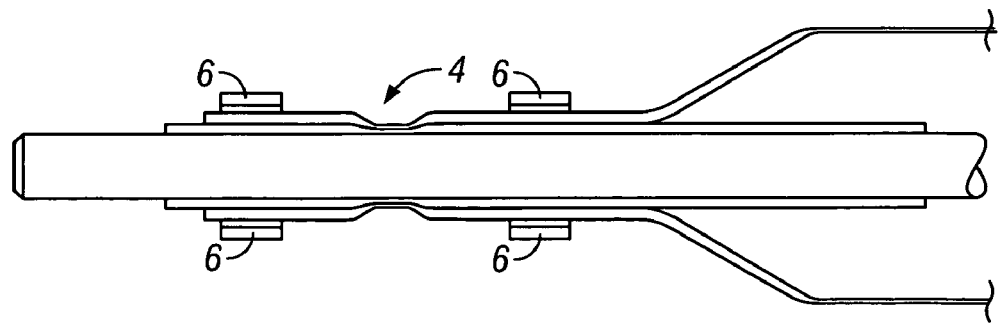
FIG. 3 shows the catheter shaft and balloon when clamped together.

However, the present invention reduces this radial swelling by applying a tensile force, such as stretching, to the welded area. As shown in FIG. 3, clamps (6) grip the balloon neck on either side of the weld zone and a tensile force is applied via the grip clamps (6). The force range is 0.75–1.5 pounds force (lbf) for a weld between a Nylon balloon and an inner shaft coextrusion of Polyethylene and PEBAX® polyether block amide copolymer by Ato Fina Chemicals, Inc. This tensile force causes the welded zone to stretch in a longitudinal direction and to shrink in a radial direction. When the polymer chains in the plastics material are heated, they relax and randomise. This results in a tendency to shrink in the direction of chain orientation and a tendency to swell in other directions. As a tensile force is applied to the region, the polymer chains reorientate in a longitudinal direction, which results in a reduction in thickness in the radial direction because the polymer chains rotate and move into a longitudinal orientation.

Figure 4:
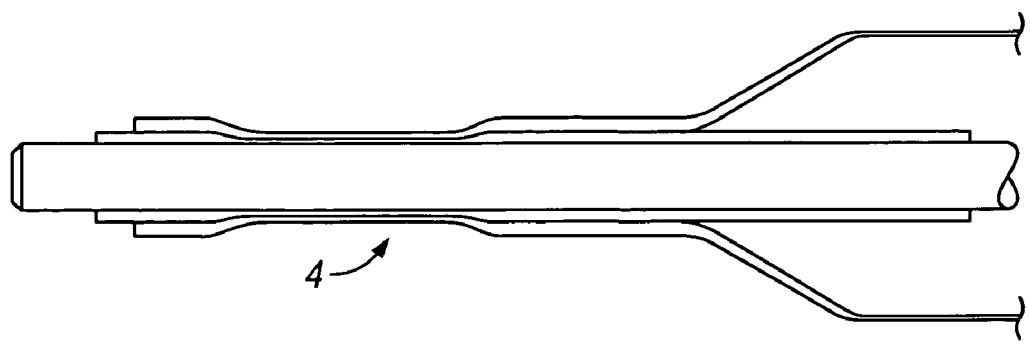
FIG. 4 shows the catheter shaft and balloon when heated and stretched in accordance with the present invention.
Figure 5:
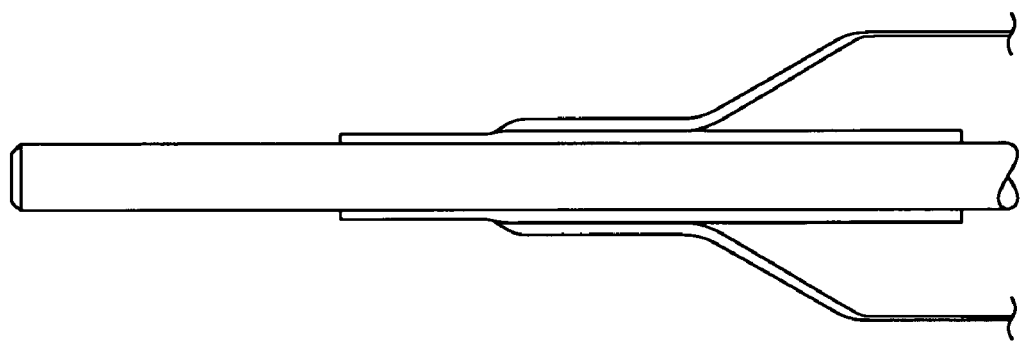
FIG. 5 shows the weld zone after cutting.

Strain hardening of the material in the direction of strain ensures that the process occurs smoothly and evenly over the length of the weld until the entire welded region has necked to the same degree, as shown in FIG. 4. Good adhesion of the weld interface ensures that both materials elongate simultaneously and to the same degree. There is little or no plastic deformation adjacent the weld area, since longitudinal orientation is still present in these areas and the longitudinal yield modulus in this area is higher than that in the weld zone. As a result, the weld area is much smaller in cross-section than the initial welded area and the polymer chains are orientated in a direction of strain. This is advantageous in the case of joints between balloons and catheter shafts, in an angioplasty catheter where it is desired to have longitudinal strength and low cross-sectional area in the welded region. A smooth taper develops at the limits of the welded region, which is also advantageous in an angioplasty catheter, since the weld zone can be cut as shown in FIG. 5 to leave a gradually tapered welded zone at the tip of the catheter.

Figure 6:
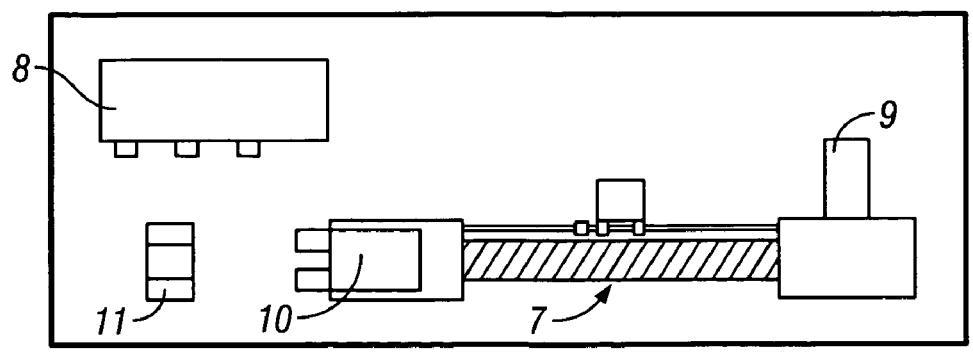
FIG. 6 shows a cold-necking machine for use in post-weld necking a joint.

A cold necking machine was developed to provide control and repeatability in the cold necking process. The machine is shown in FIG. 6 and consists of a linear motion slide (7) with an X-axis movement, the slide (7) having a speed controller (8) and DC motor (9). The machine also has two pneumatic gripper cylinders complete with removable jaws (10, 11). One jaw (10) is moveable and the other (11) is fixed. A set of micro switches controls the travel distance of the slide mechanism.

To stretch a joint between a balloon and a catheter shaft the machine is set into the home position and the jaw gaps set to an appropriate distance for the application. The distal end of the balloon is placed between the ends of the jaws (10, 11) with the extended tip between the jaws of the moving slide (7) and the jaws (10, 11) are activated to clamp the product. The machine is then started and allowed to cycle. The jaws (10) on the moving slide (7) travel away from the fixed jaws (11) to produce the necking process. The machine automatically stops when it has travelled the appropriate distance. The jaws are released, the product removed and the machine reset.

The machine is set with a travel distance of 1 to 15 mm (nominal 5 mm), a speed pot setting of 125 to 500 (nominal 275) and an air pressure of 3 to 6 bar (nominal 5 bar).

The process thus produces a reduced cross-sectional area in the welded region between the catheter and balloon, it reorientates the polymer chains in the direction of strain, it increases the flexibility of the welded section and it eliminates any swelling in the weld region which would have taken place due to polymer relaxation during the welding process.

Post-weld necking as described herein, of a welded joint can be described as the application of tensile strain to an area of a polymer assembly which has been welded, in order to 'neck' or thin out the area which has been welded.

The words "comprises/comprising" and the words "having/including" when used herein with reference to the present invention are used to specify the presence of stated features, integers, steps or components but does not preclude the presence or addition of one or more other features, integers, steps, components or groups thereof.

The invention claimed is:

1. A process for forming a joint between a polymeric balloon and a polymeric catheter shaft comprising the following steps in order:
   assembling the balloon on the shaft such that a balloon neck area overlaps the shaft;
   welding the neck area to the shaft to create a joint; and
   applying a tensile force to the joint, the force being sufficient to elongate the joint, thus thinning the joint.

2. A process as claimed in claim 1 wherein the force applied is in the range of 0.75–1.5 pounds force (lbf).

3. A process as claimed in claim 1 wherein applying a tensile force further comprises gripping the balloon neck area with clamps on either side of the joint, and applying the tensile force between the clamps.

4. A process as claimed in claim 1 wherein the tensile force is applied to a cold joint.

5. A process as claimed in claim 1 wherein the tensile force is applied to a heated joint.

6. A process as claimed in claim 5 wherein the joint is heated by the application of hot air.

7. A process as claimed in claim 1 wherein welding the neck area to the shaft further comprises heating the neck area.

8. A process as claimed in claim 1 wherein assembling the balloon on the shaft further comprises mounting the balloon and the shaft on a mandrel.

9. A process as claimed in claim 1 wherein applying a tensile force to the joint further comprises thinning the joint to a reduced cross sectional area having smooth tapers at the limits of the joint.

10. A process as claimed in claim 9 further comprising, after applying a tensile force to the joint, cutting the joint to leave a gradually tapered catheter tip.

* * * * *